(12) United States Patent
Kawanabe et al.

(10) Patent No.: US 11,759,485 B2
(45) Date of Patent: Sep. 19, 2023

(54) COMPOSITION FOR ENHANCING IMMUNE CHECKPOINT BLOCKADE THERAPY

(71) Applicant: MEIJI CO., LTD., Tokyo (JP)

(72) Inventors: Hirotaka Kawanabe, Tokyo (JP); Marie Nakamura, Tokyo (JP)

(73) Assignee: MEIJI CO., LTD., Tokyo (JP)

( * ) Notice: Subject to any disclaimer, the term of this patent is extended or adjusted under 35 U.S.C. 154(b) by 0 days.

(21) Appl. No.: 17/058,329

(22) PCT Filed: Jun. 13, 2019

(86) PCT No.: PCT/JP2019/023470
§ 371 (c)(1),
(2) Date: Nov. 24, 2020

(87) PCT Pub. No.: WO2019/240218
PCT Pub. Date: Dec. 19, 2019

(65) Prior Publication Data
US 2021/0213077 A1     Jul. 15, 2021

(30) Foreign Application Priority Data

Jun. 14, 2018 (JP) ................. 2018-113758

(51) Int. Cl.
A61K 35/747 (2015.01)
A61P 37/04 (2006.01)
A61K 35/20 (2006.01)

(52) U.S. Cl.
CPC ............ *A61K 35/747* (2013.01); *A61K 35/20* (2013.01); *A61P 37/04* (2018.01)

(58) Field of Classification Search
None
See application file for complete search history.

(56) References Cited

U.S. PATENT DOCUMENTS

| 2012/0276245 | A1* | 11/2012 | Sieuwert et al. | C12N 1/38 435/244 |
| 2018/0140665 | A1  | 5/2018  | Giacalone       |                    |
| 2019/0209623 | A1* | 7/2019  | Lu              | A61K 35/74         |
| 2019/0307140 | A1* | 10/2019 | Furuichi        | C12N 1/20          |

FOREIGN PATENT DOCUMENTS

| JP | 9-30981 | 2/1997 |
| JP | 2000-247895 | 9/2000 |
| JP | 2004-317656 | 11/2004 |
| JP | 2005-194259 | 7/2005 |
| JP | 2008-245576 | 10/2008 |
| JP | 2010-130954 | 6/2010 |
| JP | 2012-211196 | 11/2012 |
| JP | 2016-128399 | 7/2016 |
| JP | 2017-533882 | 11/2017 |
| JP | 2017-538669 | 12/2017 |
| JP | 2018064521 A * | 4/2018 |
| JP | 2018-512046 | 5/2018 |
| JP | 2021-517587 | 7/2021 |
| WO | 2011/065300 | 6/2011 |
| WO | 2015/133638 | 9/2015 |
| WO | 2016/063233 | 4/2016 |
| WO | 2016/063263 | 4/2016 |
| WO | 2016/168853 | 10/2016 |
| WO | 2016/196605 | 12/2016 |
| WO | 2016/203223 | 12/2016 |
| WO | 2017/167213 | 10/2017 |
| WO | 2017/183595 | 10/2017 |
| WO | 2018/222969 | 12/2018 |
| WO | 2019/009438 | 1/2019 |
| WO | 2019/137384 | 7/2019 |

OTHER PUBLICATIONS

Balansky et al. Cancer Lett. 147:125-137, 1999.*
Zhang et al. Brazilian Journal of Microbiology (2011) 42:1470-1478.*
Nishimura-Uemura et al. Food Microbiology 20 (2003) 267-273.*
Kanamarlapudi et al. BioMed Research International, vol. 2017, Article ID 4201809, 11 pages, 2017. https://doi.org/10.1155/2017/4201809.*
Purohit et al. J. Dairy Sci. 92:847-856, 2009.*
International SearchReport issued Sep. 17, 2019 in International (PCT) Application No. PCT/JP2019/023470 with English-language translation.
International Preliminary Report on Patentability and Written Opinion of The Searching Authority issued Dec. 15, 2020 in International (PCT) Application No. PCT/JP2019/023470 with English-language translation.
Makino, et al., "Application of exopolysaccharides (EPS produced from Lactobacillus delbrueckii ssp. bulgaricuz, and studies on increasing the production of EPS.", Japanese Journal of Lactic Acid Bacteria, 2013, vol. 24, No. 1, pp. 10-17, with English Abstract.
Kanbe, et al., "Physiological Activities of Exuacellular Polysaccharide Produced by Lactic Acid Bacteria", Japanese Journal of Dairy and Food Science, 1981, vol. 30, No. 6, pp. 219-225, with partial English translation (part of the red frame).
Makino, et al., "Mechanisms of immuno stimulatory effects exerted by yogurt fermented with strain OLL1073R-1", Lecture abstracts of conference of Japan Society of Bioscience, Biotechnology, and Agrochemistry, 2018, vol. 2018, No. 2B05p04, with English-language translation.
Kondo, et al., "Functional expression of chemokine receptor CCR6 on human effector memory CD8+ T cells", European Journal of Immunology, 2007, vol. 37, No. 1, pp. 54-65.
Yang, et al., "Impact of exopolysaccharide from Lactobacillus casei on production of FKN, MIP-3a and bone marrow-derived dendritic cell receptors fromBalb/c mice", Immunological Journal, 2012, vol. 28, No. 9, pp. 783-786, with English Abstract.

(Continued)

*Primary Examiner* — Oluwatosin A Ogunbiyi
(74) *Attorney, Agent, or Firm* — Wenderoth, Lind & Ponack, L.L.P.

(57) ABSTRACT

The object of the invention is to provide a composition for enhancing an immune checkpoint blockade therapy. A composition for enhancing an immune checkpoint blockade therapy, which contains an exopolysaccharide of a lactic acid bacterium is provided. Preferred examples of the lactic acid bacterium include *Lactobacillus* bacteria (especially *Lactobacillus delbrueckii* subsp. *bulgaricus* OLL1073 R-1).

13 Claims, 4 Drawing Sheets

(56) References Cited

OTHER PUBLICATIONS

Belkacem, et al., "Lactorbacillusparacasei feeding improves immune control of influenza infection in mice", Plos One, 2017, vol. 12, No. 9, e0184976, pp. 1-20.
Sivan et al., "Commensal Bifidobacterium promotes antitumor immunity and facilitates anti-PD-L1 efficacy", Science, 2015, 350 (6264), pp. 1084-1089.
Office Action dated Jun. 14, 2023 issued in corresponding Chinese Patent Application No. 201980039616.0, with English Machine Translation, 14 pages.
Office Action dated Jul. 18, 2023 in corresponding Japanese Patent Application No. 2020-525651, with English Machine Translation, 14 pages.

* cited by examiner

COMPOSITION FOR ENHANCING IMMUNE CHECKPOINT BLOCKADE THERAPY

TECHNICAL FIELD

The present invention relates to a composition comprising a culture of a lactic acid bacterium for enhancing an immune checkpoint blockade therapy.

BACKGROUND ART

It has been found that many kinds of tumors use an immunosuppression function based on an immune checkpoint molecule in order to avoid attacks from the immune system. The immune checkpoint blockade therapy is a therapy consisting of canceling suppression of activation of immunocytes including T lymphocytes by inhibiting transfer of immunosuppression signals by immune checkpoint molecules, and thereby increasing patient's immune activity to obtain an antitumor effect. As immunity checkpoint blockades (inhibitors), PD-1 (Programmed Death-1) blocking antibody agents, CTLA-4 (Cytotoxic T Lymphocyte-associated Antigen 4) blocking antibody agents, and so forth have been so far approved for specific tumors.

Uses of the immune checkpoint blockades in combination with other active ingredients are also examined. For example, Patent document 1 discloses a combination of one or more kinds of anticancer antibodies, and a specific immuno-adjuvant compound for treatment of cancer, and describes that this combinatory drug can be administered further in combination with an antibody that blocks an immunosuppression function. Patent document 2 discloses a peptide consisting of a straight chain sequence of nine amino acids as a compound to be used for treatment of a tumor by being administered in combination with, sequentially with, or separately from an immunity checkpoint blockade. Patent document 3 discloses a concomitant use of a compound that blocks an interaction between the signal regulatory protein alpha (SIRPa) and at least one of the ligands thereof (for example, anti-SIRPa antibody) with a second therapeutic drug, which is for use in a treatment of an arbitrary pathological condition that can be improved or prevented by differentiation of myeloid-derived suppressor cells (MDSC) into non-suppressor cells. This patent document describes that the second therapeutic drug can be selected from the group consisting of chemotherapeutic drug, radiotherapy, surgical operation, immunotherapy drug, antibiotic, and probiotics.

Meanwhile, lactic acid bacteria produce various substances in the fermentation processes thereof, and one class of them is constituted by extracellular polysaccharides (exopolysaccharides, EPSs). There are known several physiological activities of EPSs of lactic acid bacteria, such as autoimmune disease prevention action (Patent document 4), NK cell activation action (Patent document 5), pneumococcal infection prevention action (Patent document 6), fatigue feeling-improving action (Patent document 7), and action of suppressing acquired immunity hypofunction caused by an anti-influenza drug (Patent document 8).

PRIOR ART REFERENCES

Patent Documents

Patent document 1: Japanese Patent Unexamined Publication (KOKAI) No. 2012-211196
Patent document 2: Japanese Patent Unexamined Publication (KOKAI) No. 2016-128399
Patent document 3: Japanese Patent Unexamined Publication (KOHYO) No. 2017-538669
Patent document 4: Japanese Patent Unexamined Publication (KOKAI) No. 2000-247895
Patent document 5: Japanese Patent Unexamined Publication (KOKAI) No. 2005-194259
Patent document 6: International Patent Publication WO2011/065300
Patent document 7: International Patent Publication WO2015/133638
Patent document 8: International Patent Publication WO2017/183595

SUMMARY OF THE INVENTION

Object to be Achieved by the Invention

Since the immune checkpoint blockade therapy retracts tumors by activating the patients' own immunity, the patients suffer from less burden compared with the conventional surgical resection and radiotherapy. If there is a composition that can enhance the effect of this therapy, it is much more desirable.

Means for Achieving the Object

When the inventors of the present invention orally administered yogurt produced by fermentation by a *Lactobacillus* bacterium (*Lactobacillus delbrueckii* subsp. *bulgaricus* OLL1073 R-1) or exopolysaccharides obtained from the lactic acid bacterium to colon cancer model mice, the effects of the CTLA-4 blockade therapy and the PD-1 blockade therapy were enhanced, and suppression of tumor growth was observed. Further, more CCR6-positive CD8+ T lymphocytes were observed in the subjects. The present invention was accomplished on the basis of such findings.

The present invention provides the followings.

[1] A composition for enhancing an immune checkpoint blockade therapy, the composition comprising an exopolysaccharide of a lactic acid bacterium.
[2] The composition according to 1, wherein the immune checkpoint blockade therapy is a CTLA-4 (Cytotoxic T-Lymphocyte-associated Antigen 4) blockade therapy or a PD-1 (Programmed Death-1) blockade therapy.
[3] The composition according to 1 or 2, wherein the lactic acid bacterium is one classified into the genus *Lactobacillus*.
[4] The composition according to any one of 1 to 3, wherein the lactic acid bacterium is one classified into *Lactobacillus delbrueckii* subsp. *bulgaricus*.
[5] The composition according to any one of 1 to 4, which is fermented milk.
[6] A composition for increasing CCR6-positive CD8+ T lymphocytes, the composition comprising an exopolysaccharide of a lactic acid bacterium.
[7] A non-medical method for enhancing an immune checkpoint blockade therapy, making a subject ingest a composition comprising an effective amount of an exopolysaccharide of a lactic acid bacterium.
[8] A non-medical method for increasing CCR6-positive CD8+ T lymphocytes in a subject, making a subject ingest a composition comprising an effective amount of an exopolysaccharide of a lactic acid bacterium.

[9] A method for increasing CCR6-positive CD8+ T lymphocytes, the method comprising using an exopolysaccharide of a lactic acid bacterium (except for medical practices for humans).

The present invention also provides the followings.

[10] A method for enhancing an immune checkpoint blockade therapy in a subject, the method comprising (orally) administering an exopolysaccharide of a lactic acid bacterium or a composition comprising the same to a subject (making a subject (orally) ingest an exopolysaccharide of a lactic acid bacterium or a composition comprising the same).

[11] Use of an exopolysaccharide of a lactic acid bacterium in manufacture of a composition for enhancing an immune checkpoint blockade therapy.

[12] An exopolysaccharide of a lactic acid bacterium or a composition comprising the same, for use in a method for enhancing an immune checkpoint blockade therapy.

[13] A non-therapeutic method for enhancing an immune checkpoint blockade therapy in a subject, the method comprising (orally) administering an exopolysaccharide of a lactic acid bacterium or a composition comprising the same to a subject (making a subject (orally) ingest an exopolysaccharide of a lactic acid bacterium or a composition comprising the same).

[14] Use of an exopolysaccharide of a lactic acid bacterium, which is for enhancing an immune checkpoint blockade therapy.

[15] A method for increasing CCR6-positive CD8+ T lymphocytes in a subject, which comprises the step of (orally) administering an exopolysaccharide of a lactic acid bacterium or a composition comprising the same to a subject (making a subject (orally) ingest an exopolysaccharide of a lactic acid bacterium or a composition comprising the same).

[16] Use of an exopolysaccharide of a lactic acid bacterium in manufacture of a composition for increasing CCR6-positive CD8+ T lymphocytes.

[17] An exopolysaccharide of a lactic acid bacterium or a composition comprising the same, which is for use in a method for increasing CCR6-positive CD8+ T lymphocytes.

[18] A non-therapeutic method for increasing CCR6-positive CD8+ T lymphocytes in a subject, which comprises the step of (orally) administering an exopolysaccharide of a lactic acid bacterium or a composition comprising the same to a subject (making a subject (orally) ingest an exopolysaccharide of a lactic acid bacterium or a composition comprising the same).

[19] Use of an exopolysaccharide of a lactic acid bacterium, which is for increasing CCR6-positive CD8+ T lymphocytes.

[20] A method for producing a composition for enhancing an immune checkpoint blockade therapy or for increasing CCR6-positive CD8+ T lymphocytes, which comprises the step of mixing an exopolysaccharide of a lactic acid bacterium, and a pharmaceutically acceptable additive.

Effect of the Invention

According to the present invention, an immune checkpoint blockade therapy can be effectively enhanced. According to the present invention, CCR6-positive CD8+ T lymphocytes can also be increased.

BRIEF DESCRIPTION OF THE DRAWINGS

[FIG. 1A]

The tumor volumes observed for the CTLA-4 blockade therapy group (data for all the individuals). Black solid lines indicate the data for the yogurt-administered mice, and gray broken lines indicate the data for the control mice. The Student's t-test was performed for the data obtained at the time of the last tumor volume measurement, and p values were obtained.

[FIG. 1B]

The tumor volumes observed for the CTLA-4 blockade therapy group (data for the lower half of the individuals arranged in the order of tumor volume, large to small, for both the yogurt-administered group and the control group). Black solid lines indicate the data for the yogurt-administered mice, and gray broken lines indicate the data for the control mice. The Student's t-test was performed for the data obtained at the time of the last tumor volume measurement, and p values were obtained.

[FIG. 1C]

CCR6-positive ratios of the CD8+ T lymphocytes. The results are shown in the form of average±SE.

[FIG. 1D]

The tumor volumes observed for the PD-1 blockade therapy group. Black solid lines indicate the data for the yogurt-administered mice, and gray broken lines indicate the data for the control mice.

[FIG. 2A]

The tumor volumes observed for the mice (data for all the individuals). Black solid lines indicate the data for the EPS-administered mice, and gray broken lines indicate the data for the control mice. The Student's t-test was performed for the data obtained at the time of the last tumor volume measurement, and p values were obtained.

[FIG. 2B]

The tumor volumes observed for the mice (data for the lower half of the individuals arranged in the order of tumor volume, large to small, for both the EPS-administered group and the control group). Black solid lines indicate the data for the EPS-administered mice, and gray broken lines indicate the data for the control mice. The Student's t-test was performed for the data obtained at the time of the last tumor volume measurement, and p values were obtained.

[FIG. 3]

CCR6-positive ratios of the TG40 cells (%). In the system containing EPS, the CCR6-positive ratio significantly increased ($p<0.001$) compared with the control in which EPS was not added (Student's t-test).

MODES FOR CARRYING OUT THE INVENTION

Hereafter, the present invention will be explained in detail.

The present invention relates to a composition for enhancing an immune checkpoint blockade therapy, which uses an exopolysaccharide (EPS) produced by a lactic acid bacterium as an active ingredient.

Active Ingredient

The composition of the present invention contains EPS of a lactic acid bacterium as an active ingredient.

The term lactic acid bacteria is a general term indicating microorganisms that utilize glucose to produce lactic acid at a yield of 50% or higher based on the saccharide, and as for their physiological characteristics, they are gram-positive cocci or bacilli, and show such characteristics as no motility, no sporulation ability, and catalase negativity. From ancient times, lactic acid bacteria have been eaten in every corner of the world as those contained in fermented milk, and so forth, and can be considered to be extremely safe microorganisms. The lactic acid bacteria are classified into a plurality of genera. EPS of a lactic acid bacterium contained in the composition of the present invention is preferably one produced by a *Lactobacillus* lactic acid bacterium, which is classified into the genus *Lactobacillus*.

Examples of the genus *Lactobacillus* include, for example, those of *Lactobacillus bulgaricus*, *Lactobacillus casei*, *Lactobacillus acidophilus*, *Lactobacillus plantarum*, and so forth. Among these genus *Lactobacillus*, lactic acid bacteria classified into the *bulgaricus* species (also referred to as *bulgaricus* bacteria) are preferred for the present invention. Among these genus *Lactobacillus* lactic acid bacteria, those classified into *Lactobacillus delbrueckii* subsp. *bulgaricus* are more preferred. According to a particularly preferred embodiment, the lactic acid bacterium is *Lactobacillus delbrueckii* subsp. *bulgaricus* OLL1073 R-1 strain (accession number FERM BP-10741) (also referred to as "*Lactobacillus delbrueckii* subsp. *bulgaricus* strain").

The *Lactobacillus delbrueckii* subsp. *bulgaricus* R-1 strain was deposited at the independent administrative agency, National Institute of Technology and Evaluation, International Patent Organism Depository (IPOD, NITE, #120, 2-5-8 Kazusakamatari, Kisarazu-shi, Chiba-ken, 292-0818, Japan) as an international deposition based on the provisions of the Budapest Treaty (depositor, Meiji Co., Ltd.; deposition date, Nov. 29, 2006; accession number, FERM BP-10741).

EPS to be used in the composition of the present invention as an active ingredient is not particularly limited, so long as it is an EPS that is produced by a lactic acid bacterium (preferably a *Lactobacillus* lactic acid bacterium classified into the genus *Lactobacillus*) and provides the objective effect. EPSs produced by lactic acid bacteria are structurally classified into homopolysaccharides and heteropolysaccharides (for example, those constituted by galactose and glucose), and may be modified by phosphorylation, sulfation, or the like, and those of both types can be used as the active ingredient of the composition of the present invention. One of the preferred examples is an acidic EPS containing many phosphate groups. Examples of such EPS are EPSs produced by the *Lactobacillus delbrueckii* subsp. *bulgaricus* R-1 strain (refer to Patent document 6 mentioned above).

EPS of a lactic acid bacterium contained in the composition of the present invention may be contained as a lactic acid bacterium fermentation product. The lactic acid bacterium fermentation product may be a fermentation product itself produced by a lactic acid bacterium, or a processed product thereof. The lactic acid bacterium fermentation product may be, for example, fermented milk (specifically, yogurt etc.). Examples of the processed product thereof include, for example, roughly purified product, culture filtrate or culture supernatant obtained from the fermentation product by removing cells using filtration, centrifugation, or membrane separation, concentrate obtained by concentrating the culture filtrate or culture supernatant, and dried product of the concentrate.

As for the production method of EPS of a lactic acid bacterium, Patent document 6 mentioned above, and so forth can be referred to. When EPS of a lactic acid bacterium is prepared as a lactic acid bacterium fermentation product, fermented milk containing EPS can be produced by adding a lactic acid bacterium that produces EPS as a starter to raw material milk, and allowing fermentation so that EPS is produced in the fermentation product. The conditions for the fermentation, such as type of raw material milk, fermentation temperature, and fermentation time, are not particularly limited, so long as the lactic acid bacterium used can produce EPS, and those skilled in the art can appropriately set them.

Use

The composition of the present invention can be used in order to enhance an immune checkpoint blockade therapy. The expression of to enhance an immune checkpoint blockade therapy means to make the effect of the immune checkpoint blockade therapy to be obtained earlier, to increase the effect of the immune checkpoint blockade therapy, to increase response rate for the immune checkpoint blockade therapy, to make the effect of the immune checkpoint blockade therapy to be obtained with a lower dose of the immune checkpoint blockade, or the like, when the composition of the present invention is used in combination with the immune checkpoint blockade therapy. Examples of the effect of an immune checkpoint blockade therapy include, for example, shrink of cancer by death of cancer cells (decrease of tumor volume), delay of growth of cancer (suppression of increase of tumor volume), cure of cancer, prevention of metastasis or recurrence of cancer, and death of possible metastasized cancer cells.

The immune checkpoint molecules constitute a group of molecules that suppress immune responses to self in order to maintain immunological homeostasis, and at the same time, suppress excessive immunoreactions. Although they originally exist in order to suppress excessive activation of the immunocytes including T lymphocytes, and prevent attacks against self, cancer cells utilize them in a carcinogenic process in order to avoid attacks by the immune system and thereby grow. Until now, various immune checkpoint molecules and ligands thereof have been identified.

Examples of the immune checkpoint molecules include PD-1, CTLA-4, TIM-3, BTLA, and LAG-3/TCR, and the composition of the present invention can be used in a therapy concerning inhibition by any of such immune checkpoint molecules. Especially preferred examples of the therapy include a therapy using a CTLA-4 blockade and a therapy using a PD-1 blockade. Examples of the CTLA-4 blockade include ipilimumab (Yervoy), avelumab, and atezolizumab, and examples of the PD-1 blockade include nivolumab (Opdivo), pembrolizumab (Keytruda), and pembrolizumab. The composition of the present invention can be used for any immune checkpoint blockade therapy using any of these.

The lowness of response rate for immune checkpoint blockade therapies has constituted a serious problem. The main cause for that is that many checkpoints (brakes) occur until the immune system of patient functions and cancer cells are actually injured. That is, even if one of the brakes can be eliminated with one kind of immunity checkpoint blockade, there are often still other brakes, and therefore sufficient curative effect cannot be observed in many cases. The composition of the present invention has an action of increasing a certain kind of cytotoxic T lymphocytes (CCR6-positive CD8+ T lymphocytes). Therefore, it is considered that, only by eliminating one brake of cytotoxic T lymphocytes, such as CTLA-4 and PD-1, among the checkpoints of various immunocytes, the effect was markedly increased, and the curative effect was clearly observed. This leads that the composition of the present invention can also be expected to compensate the lowness of the response rate for immune checkpoint blockade therapies.

Examples of cancers to which immune checkpoint blockade therapy is applied include malignant melanoma, nonsmall cell lung cancer, renal cell cancer, Hodgkin's lymphoma, head and neck cancer, gastric cancer, urinary tract epithelial cancer, Merkel cell cancer, and so forth. The composition of the present invention can be used for an immune checkpoint blockade therapy for any of these.

According to the study of the inventors of the present invention, when the composition of the present invention was administered, increase in CCR6-positive CD8+ T lymphocytes was observed in a target tumor, and growth of the tumor was suppressed. Further, when T lymphocytes-derived cell strain TG40 was cultured with EPS, CCR6-positive ratio increased compared with the control not using EPS. These results suggested a possibility that EPS would directly increase CCR6-positive ratio of T lymphocytes. That is, it was found that the composition of the present invention has an action of helping the action of CCR6-positive CD8+ T lymphocytes to recognize and kill cells as foreign matter for the subject (cancer cells, virus-infected cells, etc.) (for example, increasing the T lymphocytes, promoting guidance to foreign matter, etc.). Therefore, the composition of the present invention can be used for increasing CCR6-positive CD8+ T lymphocytes in the body of a subject, and it can be used for increasing CCR6-positive CD8+ T lymphocytes especially in a tumor in the body of the subject. The CCR6-positive ratio means a ratio of CCR6-positive cells among T lymphocytes, unless especially indicated. The CCR6-positive ratio can be obtained as (number of CD3+, CD8+, and CCR6-positive cells)/(number of CD3+ and CD8+ cells), and for an experiment system using TG40, the CCR6-positive ratio can be obtained as (number of CCR6-positive cells)/(total number of TG40 cells).

The composition of the present invention can be used even for a case that the immune checkpoint blockade therapy is carried out together with another therapy for treatment of cancer. Examples of such another therapy include operation (surgical treatment), therapy using a drug other than immune checkpoint blockade (for example, antimetabolite, alkylating agent, anticancerous antibiotic, microtubule inhibitor, etc.), radiotherapy, hematopoietic stem cell transplantation after a pre-transplantation treatment consisting of massive chemotherapy, systemic radiotherapy, or the like, immunotherapy other than immune checkpoint blockade therapy (for example, cytokine therapy, administration of an immunostimulator, immunocyte transplantation, etc.), alternative therapy for cancer using health food or supplement, and so forth.

Composition

Food Composition Etc.

The composition of the present invention can be in the form of a food composition or pharmaceutical composition. Food and drug are not limited to those for humans, and may be those for animals other than human, unless especially indicated. The food may be a common food, functional food, or nutritional composition, or a therapeutic diet (diet for the purpose of treatment, for which a medical practitioner writes a dietary prescription, and which is cooked by a dietitian or the like according to the prescription), dietetic food, ingredient-modified food, care food, or treatment-supporting food, unless especially indicated. The food is not limited to a solid food, but it may be a food in the form of liquid, for example, drink, drinkable preparation, liquid food, or soup, unless especially indicated. Functional food refers to a food that can give a predetermined functionality to a living body, and includes health foods at large, such as foods for specified health uses (abbreviated as "Tokuho" in Japanese, including conditional foods for specified health use), foods with function claims, foods with health claims including foods with nutrient function claims, foods for special dietary uses, supplements (for example, those of various kinds of dosage forms such as tablet, coated tablet, sugar-coated tablet, capsule and solution), and cosmetic food (for example, diet foods). In the present invention, the "functional foods" include health foods to which the health claim based on the food standards of CODEX (JOINT FAO/WHO FOOD STANDARDS PROGRAMME CODEX ALIMENTARIUS COMMISSION) is applied.

Object

The composition of the present invention is suitable to be ingested by or administered to a subject who or which receives an immune checkpoint blockade therapy, or a subject who or which is planned to receive an immune checkpoint blockade therapy.

Administration Route

Although the composition of the present invention may be administered parenterally, for example, by tube administration (by gastric fistula, cecal fistula, or the like), or may be administered nasally or orally, it is preferably orally administered.

Content and Dose of Active Ingredient

Content of EPS of a lactic acid bacterium in the composition of the present invention may be such an amount that the objective effect can be exhibited. Although the dose or ingestion amount of the composition can be appropriately determined in consideration of various factors such as age, weight, and condition of the subject, the daily administration or ingestion amount of EPS of a lactic acid bacterium may be, for example, 0.1 mg or larger, and it is preferably 0.6 mg or larger, more preferably 3 mg or larger. No matter how the minimum daily amount of EPS is defined, the maximum daily amount of EPS may be 480 mg or smaller, and it is preferably 360 mg or smaller, more preferably 180 mg or smaller, particularly preferably 90 mg or smaller.

The amount of EPS of a lactic acid bacterium per one time of administration or meal, i.e., dose of EPS for single administration or meal, may be, for example, 0.03 mg or larger, and it is preferably 0.2 mg or larger, more preferably 1 mg or larger. No matter how the minimum amount of EPS for single administration or meal is defined, the maximum amount of the same may be 160 mg or smaller, and it is preferably 120 mg or smaller, more preferably 60 mg or smaller, particularly preferably 30 mg or smaller.

When fermented milk is used as EPS of a lactic acid bacterium of the composition of the present invention, the daily amount of the fermented milk may be, for example, 10 g or larger, and it is preferably 30 g or larger, more preferably 60 g or larger. No matter how the minimum daily amount of fermented milk is defined, the maximum amount of the same may be, for example, 1500 g or smaller, and it is preferably 1200 g or smaller, more preferably 600 g or smaller.

The amount of fermented milk for one time of administration or meal, i.e., dose for single administration or meal, may be, for example, 3 g or larger, and it is preferably 10 g or larger, more preferably 20 g or larger. No matter how the minimum amount of fermented milk for one time of administration or meal is defined, the maximum amount of the same may be, for example, 800 g or smaller, and it is preferably 400 g or smaller, more preferably 200 g or smaller.

The composition may be administered or ingested one time per day; or may be administered a plurality of times per day, for example, at every meal, i.e., three times a day. The composition uses EPS of a lactic acid bacterium, which has been abundantly used in foods for many years, as the active ingredient. Therefore, the composition of the present invention can be ingested repetitively, or over a long period of time, and it may be continuously administered or ingested over, for example, one week or longer, preferably four weeks or longer.

Other Ingredients and Additives

The composition of the present invention may contain another active ingredient or nutritional ingredient acceptable for foods or drugs. Examples of such an ingredient include amino acids (for example, lysine, arginine, glycine, alanine, glutamic acid, leucine, isoleucine, and valine), saccharides (glucose, sucrose, fructose, maltose, trehalose, erythritol, maltitol, paratinose, xylitol, and dextrin), electrolytes (for example, sodium, potassium, calcium and magnesium), vitamins (for example, vitamin A, vitamin B1, vitamin B2, vitamin B6, vitamin B12, vitamin C, vitamin D, vitamin E, vitamin K, biotin, folic acid, pantothenic acid, and nicotinic acid), minerals (for example, copper, zinc, iron, cobalt, and manganese), antibiotics, dietary fibers, proteins, lipids, and so forth.

The composition may also further contain an additive acceptable for foods or drugs. Examples of such an additive include inactive carriers (solid and liquid carriers), excipients, surfactants, binders, disintegrating agents, lubricants, dissolving aids, suspending agents, coating agents, colorants, preservatives, buffering agents, pH adjustors, emulsifiers, stabilizers, sweeteners, antioxidants, perfumes, acidulants, and natural substances. More specific examples include water, other aqueous solvents, pharmaceutically acceptable organic solvents, collagen, polyvinyl alcohol, polyvinylpyrrolidone, carboxyvinyl polymer, sodium alginate, water-soluble dextran, water-soluble dextrin, carboxymethyl starch sodium, pectin, xanthan gum, gum arabic, casein, gelatin, agar, glycerin, propylene glycol, polyethylene glycol, vaseline, paraffin, stearyl alcohol, stearic acid, human serum albumin, mannitol, sorbitol, lactose, sucralose, stevia, aspartame, acesulfame potassium, citric acid, lactic acid, malic acid, tartaric acid, phosphoric acid, acetic acid, fruit juice, vegetable juice, and so forth.

Dosage Form or Shape

The pharmaceutical composition of the present invention can be in an arbitrary dosage form suitable for oral administration, for example, solid preparation such as tablet, granule, powder, pill, and capsule, liquid preparation such as solution, suspension, and syrup, gel, aerosol, or the like.

The food composition of the present invention may be prepared in an arbitrary form such as solid, liquid, mixture, suspension, powder, granule, paste, jelly, gel, and capsule. The food composition of the present invention can be made in such an arbitrary form as dairy product, supplement, confectionery, drink, drinkable preparation, seasoning, processed food, daily dish, and soup. More specifically, the composition of the present invention may be in the form of milk beverage, soft drink, fermented milk, yogurt, ice cream, tablet, cheese, bread, biscuit, cracker, pizza crust, special formula powdered milk, liquid food, food for sick persons, nutritional food, frozen food, processed food, or the like, or may be in a form for being mixed in drink or food and then ingested, such as granule, powder, paste, and thick solution.

Others

In the manufacture of the composition of the present invention, time of adding EPS of a lactic acid bacterium can be appropriately chosen. Unless the characteristics of EPS of a lactic acid bacterium are not markedly degraded, the time of the addition is not particularly limited. For example, it can be added to the raw materials and mixed in an early stage of the manufacture. Alternatively, when the composition of the present invention is implemented as fermented milk, fermented milk containing EPS can be produced by adding a lactic acid bacterium that produces EPS as a starter to raw material milk, and allowing fermentation so that EPS is produced.

The composition of the present invention can have an indication describing that the composition can be used for enhancing an immune checkpoint blockade therapy, or an indication describing that ingestion of the composition is recommended for specific subjects. The indications may be a direct or indirect indication. Examples of the direct indication include descriptions on tangible articles such as the product itself, package, container, label, and tag, and examples of the indirect indication includes advertising campaign activities using such places or means as web site, shop, pamphlet, exhibition, book, newspaper, magazine, television, radio, postal matter, E-mail, and sound.

Hereafter, the present invention will be more specifically explained with reference to examples. However, the technical scope of the present invention is not limited by these examples.

EXAMPLES

Preparation of Yogurt and EPS (Exopolysaccharide)

In Example 1, yogurt prepared by adding *Lactobacillus delbrueckii* subsp. *bulgaricus* OLL1073 R-1 and *Streptococcus thermophilus* as a lactic starter to a skim milk powder medium, and allowing fermentation of the skim milk powder medium for 2.5 hours in a temperature environment of 43° C. was used. In Examples 2 and 3, EPS contained in a culture obtained by culturing the *Lactobacillus delbrueckii* subsp. *bulgaricus* OLL1073 R-1 in a 10 mass % skim milk powder medium was purified. That is, trichloroacetic acid was added at a final concentration of 10 mass % to the aforementioned culture in which cultivation was performed at 37° C. for 18 hours, denatured proteins were removed, cold ethanol was added to the culture, and the mixture was left standing at 4° C. for 2 hours to obtain precipitates containing EPS. The precipitates were dialyzed against MilliQ water by using a dialysis membrane (molecular cutoff, 6 to 8 kDa), nucleic acids and proteins were enzymatically decomposed, and ethanol precipitation was performed again to obtain precipitates. The precipitates were dissolved in MilliQ water, and after dialysis is performed again, they were lyophilized to purify EPS.

Example 1

Thirty-two in total of 7 weeks old BALB/c male mice (Charles River Japan) were divided into groups of control mice (n=16) and yogurt administration mice (n=16). To the control mice and yogurt administration mice, 400 μL/animal of 10% (w/v) skim milk powder solution and the yogurt were orally administered, respectively. The oral administration was carried out once a day every day until the day before the dissection. The amount of EPS contained in 400 μL of the yogurt was 28 μg as determined by HPLC using a corona charged particle detector.

On the day of the start of the oral administration, there was prepared a suspension (suspension in PBS) of the colon 26 single cells, which are cells of mouse colon cancer cell strain, and $6.0 \times 10^5$ cells/200 μL were subcutaneously transplanted to each of all the mice on the left abdomen using 26G injection hypodermic needle (TERUMO). The mice of each group (n=16) were further divided into 2 groups according to the treatment method, one of which was CTLA-4 blockade therapy group (n=8), and the other of which was PD-1 blockade therapy group (n=8). Each therapeutic drug (anti-mouse CTLA-4 antibody or anti-mouse PD-1 antibody) was intraperitoneally administered 3 times (150 μg/animal/time) until 10 days after the tumor transplantation in the case of the CTLA-4 blockade therapy group, or 5 times (240 μg/animal/time) until 18 days after the tumor transplantation in the case of the PD-1 blockade therapy group.

Follow-up was performed by measuring the tumor volume with a ruler 3 times per week. In the case of the CTLA-4 blockade therapy group, the mice were dissected 15 days after the tumor transplantation, and the tumor-infiltrating T lymphocytes were analyzed and compared. In the case of the PD-1 blockade therapy group, when the tumor volume exceeded 2000 mm$^3$, which was defined as a humane endpoint, the mice were euthanized at each occasion.

Figure 1A:
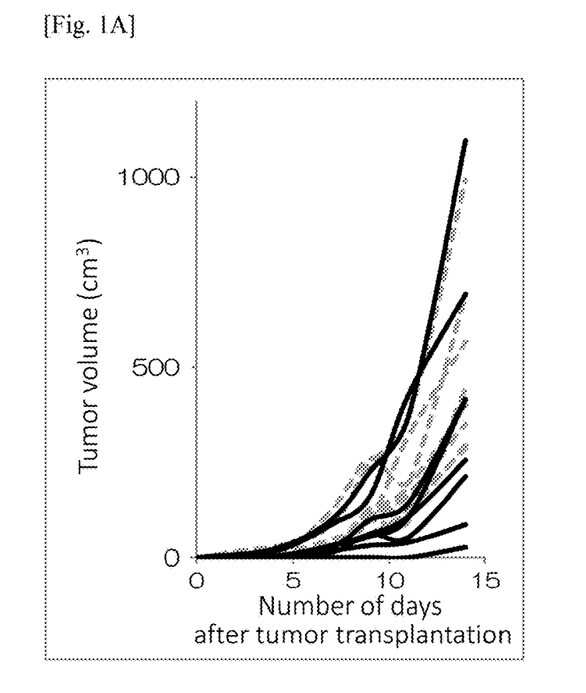
Figure 1B:
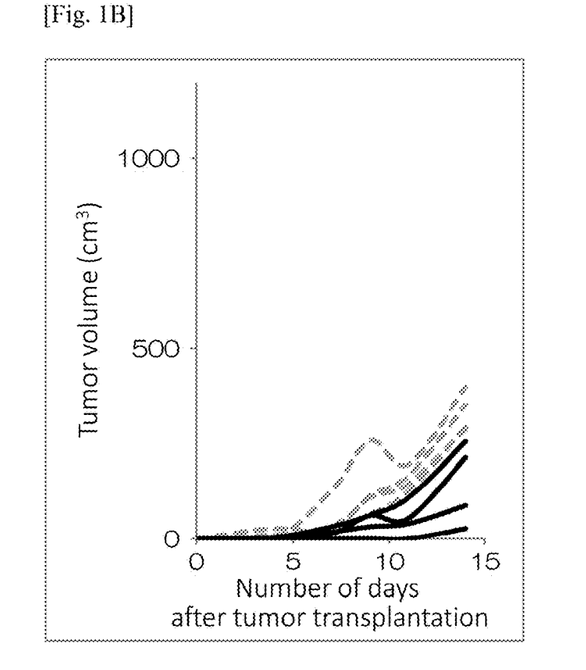

In the CTLA-4 blockade therapy group, significant difference was not observed in comparison of the tumor volumes of the mice of the both groups observed immediately before the dissection (FIG. 1A). However, when there were compared the tumor volumes of the mice of half numbers of the groups, which showed lower tumor volumes, and thus in which the therapeutic effect of the drug was considered to be observed, the tumor volumes of the yogurt-administered mice were significantly smaller than those of the control mice (FIG. 1B).

Further, each of the extracted tumor masses was minced with a scalpel, and incubated (37° C., 1 hour) in the RPMI 1640 medium containing collagenase (Roche) and DNase (Roche) to obtain a single cell suspension. These cells were stained with an antibody mix containing fluorescence-labeled anti-mouse CD3 antibody, anti-mouse CD8 antibody, and anti-mouse CCR6 antibody (all from Japan BD), and the tumor-infiltrating T lymphocytes were analyzed by using a flow cytometer (FACS Verse, Japan BD).

Figure 1C:
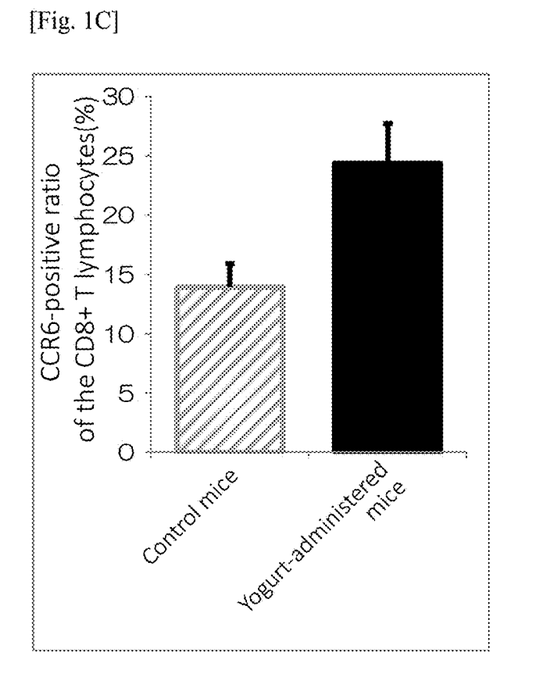

As a result, it was found that the CCR6-positive CD8+ T lymphocytes significantly increased in the yogurt-administered mice (FIG. 1C). It was confirmed by this result that the cell-mediated immunity was activated in the cancer tissues to suppress the growth of the tumor in the yogurt-administered mice.

Figure 1D:
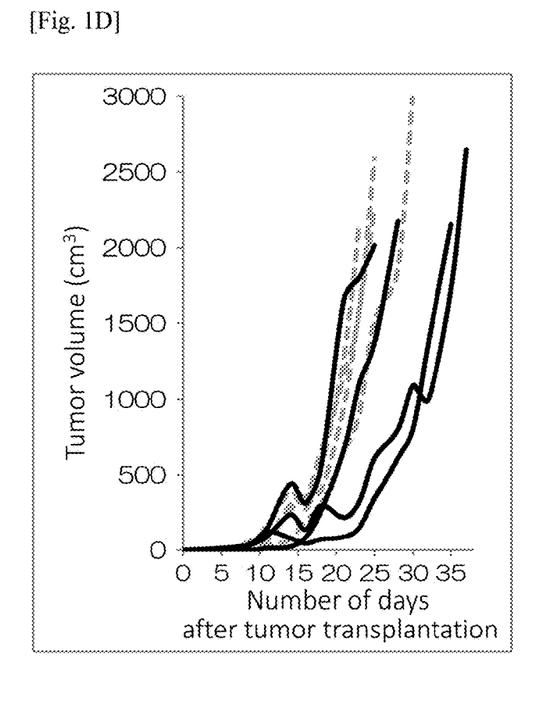

When the tumor growth of the mice of the both groups of the PD-1 blockade therapy group was followed up, individuals in which tumor growth was clearly suppressed during the drug administration period (until 18 days after the tumor transplantation) were observed only in the yogurt-administered mouse group (FIG. 1D).

The above results revealed that oral ingestion of yogurt of the present invention or EPS contained in it enhances the therapeutic effect of the CTLA-4 blockade therapy or the PD-1 blockade therapy.

Example 2

Twenty-four in total of 7 weeks old BALB/c male mice (Charles River Japan) were divided into groups of control mice (n=12) and EPS administration mice (n=12). The control mice and yogurt administration mice were allowed to freely drink distilled water and an EPS aqueous solution (25 μg/ml), respectively (it was recognized that the mice drunk about 4 to 8 mL/day of water or the solution), until the day of dissection.

On the day of the start of the free drinking, a colon 26 single cell suspension (suspension in PBS) was prepared, and $6.0 \times 10^5$ cells/200 μL were subcutaneously transplanted to each of all the mice on the left abdomen using 26G injection hypodermic needle (TERUMO). Anti-mouse CTLA-4 antibody was intraperitoneally administered 3 times (150 μg/animal/time) to all the mice until 10 days after the tumor transplantation. Follow-up was performed by measuring the tumor volume with a ruler 3 times per week. All the mice were dissected 15 days after the transplantation of tumor.

Figure 2A:
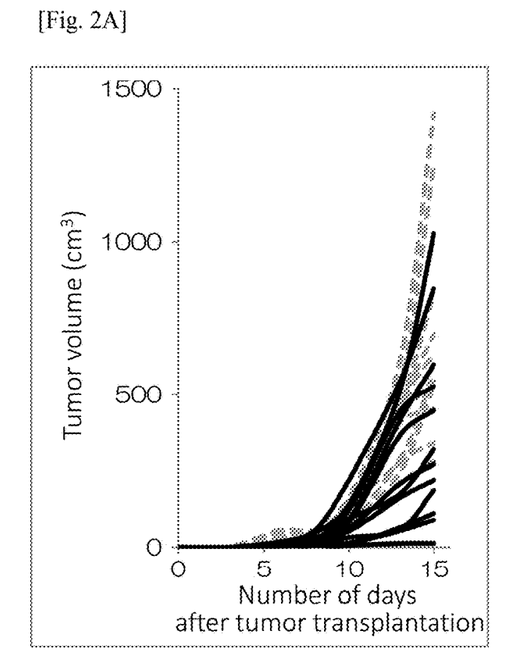
Figure 2B:
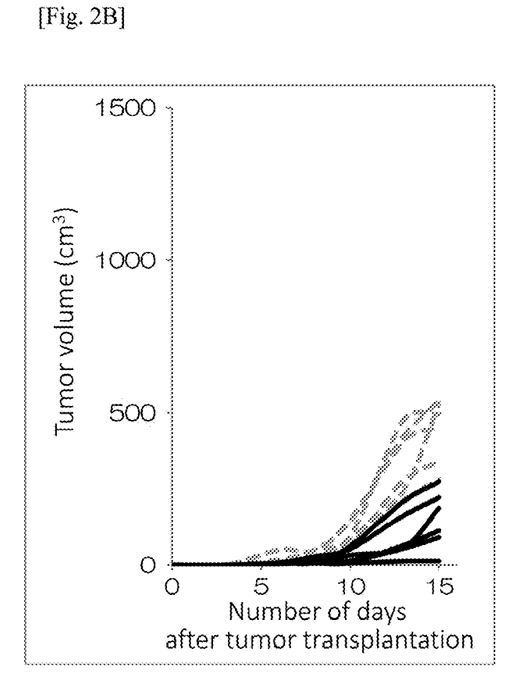

When the tumor volumes of the mice of the both groups observed immediately before the dissection day were compared, it was found that the tumor volumes observed for the EPS administration group were significantly smaller (FIG. 2A), and when the tumor volumes of the mice of half numbers of the respective groups showing smaller tumor volumes were compared, more significant tumor growth suppression was observed for the same group (FIG. 2B).

The above results revealed that oral ingestion of yogurt of the present invention or EPS contained in it enhances the therapeutic effect of the CTLA-4 blockade therapy or the PD-1 blockade therapy.

Example 3

EPS (150 μg/ml) was added to cultured cells of the cell strain TG40 (derived from mouse T lymphocytes), and the cells were cultured for 6 hours. The medium was prepared by adding fetal bovine serum (FBS) to RPMI at 10 mass percent concentration, and the cells were inoculated to the medium on a plate at a density of $5 \times 10^6$ cells/mL, and maintained at 37° C. and 5% $CO_2$.

The cells were stained with fluorescence-labeled anti-mouse CCR6 antibody, and analyzed by using a flow cytometer (FACS Verse, Japan BD).

Figure 3:
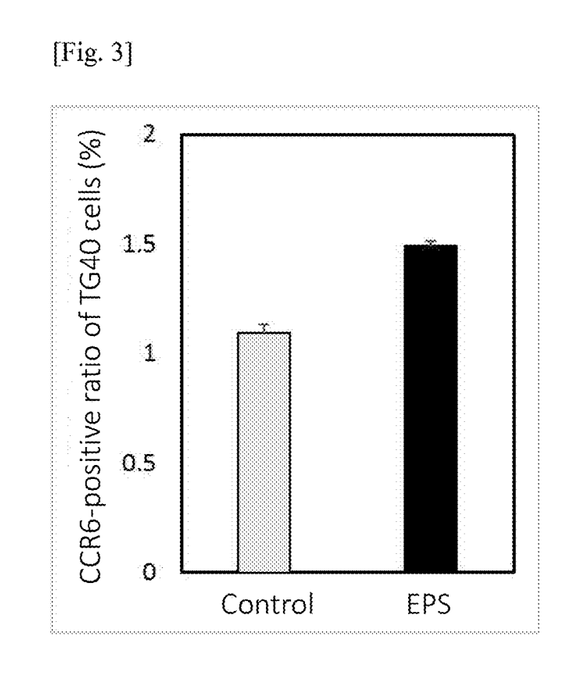

As a result, it was found that CCR6-positive ratio significantly increased (p<0.001) in the system to which EPS was added compared with the control in which EPS was not added (Student's t-test, FIG. 3). This result suggested that EPS directly increases CCR6-positive CD8+ T lymphocytes in an environment other than intratumoral environment.

The invention claimed is:

1. A method for enhancing an immune checkpoint blockade therapy, the method comprising:
   administering (i) a fermented milk comprising an effective amount of an exopolysaccharide of *Lactobacillus delbrueckii* subsp. *bulgaricus* made from milk, the fermented milk being obtained by fermenting medium containing milk in the presence of one or more kind of lactic acid bacterium comprising *Lactobacillus delbrueckii* subsp. *bulgaricus*, or (ii) an effective amount of an exopolysaccharide of *Lactobacillus delbrueckii* subsp. *bulgaricus* made from milk, the exopolysaccharide being obtained by fermenting medium containing milk in the presence of *Lactobacillus delbrueckii* subsp. *bulgaricus*, to a subject who has received an immune checkpoint blockade therapy, thereby enhancing the immune checkpoint blockade therapy, wherein the exopolysaccharide enhances the immune checkpoint blockade therapy.

2. The method according to claim 1, wherein the immune checkpoint blockade therapy is a CTLA-4 (Cytotoxic T-Lymphocyte-associated Antigen 4) blockade therapy or a PD-1 (Programmed Death-1) blockade therapy.

3. The method according to claim 1, wherein the *Lactobacillus delbrueckii* sub sp. *bulgaricus* is *Lactobacillus delbrueckii* sub sp. *bulgaricus* OLL1073 R-1 with an accession number FERM BP-10741.

4. The method according to claim 1, wherein the fermented milk is administered.

5. A method for increasing CCR6-positive CD8+T lymphocytes, the method comprising:

administering a composition comprising an effective amount of an exopolysaccharide obtained by fermenting milk in the presence of *Lactobacillus delbrueckii* subsp. *bulgaricus* to a subject who has received an immune checkpoint blockade therapy, thereby increasing CCR6-positive CD8+ T lymphocytes.

6. The method according to claim 1, wherein the fermented milk is obtained by fermenting the medium containing the milk with only one or more kind of lactic acid bacterium.

7. The method according to claim 1, wherein the fermented milk further comprises *Streptococcus thermophilus*.

8. The method according to claim 1, wherein the subject is one in which the immune checkpoint blockade therapy has been effective.

9. The method according to claim 1, wherein the exopolysaccharide is a purified, concentrated, and/or dried exopolysaccharide.

10. The method according to claim 1, wherein the medium containing milk is skim milk powder medium.

11. The method according to claim 1, wherein the milk is skim milk.

12. A method for enhancing an immune checkpoint blockade therapy, the method comprising:

administering an immune checkpoint blockade therapy to a subject having cancer, and administering (i) a fermented milk comprising an effective amount of an exopolysaccharide of *Lactobacillus delbrueckii* subsp. *bulgaricus* made from milk, the fermented milk being obtained by fermenting medium containing milk in the presence of one or more kind of lactic acid bacterium comprising *Lactobacillus delbrueckii* subsp. *bulgaricus*, or (ii) an effective amount of an exopolysaccharide of *Lactobacillus delbrueckii* subsp. *bulgaricus* made from milk, the exopolysaccharide being obtained by fermenting medium containing milk in the presence of *Lactobacillus delbrueckii* subsp. *bulgaricus*, to the subject having cancer, thereby enhancing the immune checkpoint blockade therapy, wherein the exopolysaccharide enhances the immune checkpoint blockade therapy.

13. A method for enhancing an immune checkpoint blockade therapy, the method comprising:

administering (i) a fermented milk comprising an effective amount of an exopolysaccharide of *Lactobacillus delbrueckii* subsp. *bulgaricus* made from milk, the fermented milk being obtained by fermenting medium containing milk in the presence of one or more kind of lactic acid bacterium comprising *Lactobacillus delbrueckii* subsp. *bulgaricus*, or (ii) an effective amount of an exopolysaccharide of *Lactobacillus delbrueckii* subsp. *bulgaricus* made from milk, the exopolysaccharide being obtained by fermenting medium containing milk in the presence of *Lactobacillus delbrueckii* subsp. *bulgaricus*, to a subject, in combination with an immune checkpoint blockade therapy, thereby enhancing the immune checkpoint blockade therapy, wherein the exopolysaccharide enhances the immune checkpoint blockade therapy.

* * * * *